United States Patent
Shi et al.

(10) Patent No.: US 11,802,256 B2
(45) Date of Patent: Oct. 31, 2023

(54) METHOD FOR EXTRACTING PALMITOLEIC ACID FROM MACADAMIA INTEGRIFOLIA AND USE THEREOF

(71) Applicant: SOUTHWEST FORESTRY UNIVERSITY, Kunming (CN)

(72) Inventors: Rui Shi, Kunming (CN); Can Liu, Kunming (CN); Wenlin Wang, Kunming (CN); Liang Tao, Kunming (CN); Jinchao Qiao, Kunming (CN); Siqi Li, Kunming (CN); Na Lu, Kunming (CN)

(73) Assignee: SOUTHWEST FORESTRY UNIVERSITY, Kunming (CN)

( * ) Notice: Subject to any disclaimer, the term of this patent is extended or adjusted under 35 U.S.C. 154(b) by 0 days.

(21) Appl. No.: 17/827,668

(22) Filed: May 28, 2022

(65) Prior Publication Data
US 2022/0411714 A1    Dec. 29, 2022

(30) Foreign Application Priority Data

Jun. 25, 2021 (CN) .......................... 202110710928.9

(51) Int. Cl.
| | |
|---|---|
| *C11B 1/10* | (2006.01) |
| *C11B 1/06* | (2006.01) |
| *C11C 1/02* | (2006.01) |
| *A61K 8/92* | (2006.01) |
| *A61K 31/201* | (2006.01) |
| *C11B 3/08* | (2006.01) |
| *C11B 3/12* | (2006.01) |

(52) U.S. Cl.
CPC ................ *C11B 1/10* (2013.01); *A61K 8/922* (2013.01); *A61K 31/201* (2013.01); *C11B 1/06* (2013.01); *C11B 3/08* (2013.01); *C11B 3/12* (2013.01); *C11C 1/025* (2013.01)

(58) Field of Classification Search
CPC ..... C11B 1/06; C11B 1/08; C11B 1/10; C11B 1/108; C11B 3/06; C11B 3/08; C11B 3/12; C11C 1/08; C11C 1/025
See application file for complete search history.

(56) References Cited

FOREIGN PATENT DOCUMENTS

CN         110204432 A    *  9/2019    ............. A23L 33/12

OTHER PUBLICATIONS

CN 110204432 (A) Yang Zengsong, Method for preparing palmitoleic acid from Macadamia oil and application of palmitoleic acid, English translation, 14 pages (Year: 2019).*
Chinese Standard GB/T 5009.37-2003, "Method for Analysis of Hygienic Standard of Edible Oils," Aug. 11, 2003, 11 pages, includes English Translation of the Forward.
CN Office Action from CN202110710928.9 with English Translation, dated Mar. 3, 2022, 12 pages.
Guo et al., "Determination and Correlation Analysis of Functional Components and Antioxidant Activity of Successive Solvent Extracts from Macadamia Green Hust," China Academic Journal Electronic Publishing House, vol. 42, No. 07, English Abstract Only, Mar. 10, 2020, 9 pages.

* cited by examiner

*Primary Examiner* — Yate' K Cutliff
(74) *Attorney, Agent, or Firm* — Haynes Beffel & Wolfeld LLP; Andrew L. Dunlap

(57) ABSTRACT

The present disclosure relates to the technical field of nut-derived fruit oil preparation, in particular to a method for extracting palmitoleic acid from *Macadamia integrifolia* and use thereof. In the method for extracting palmitoleic acid from *Macadamia integrifolia*, a fruit oil of the *Macadamia integrifolia* is purified by vacuum distillation, and an antioxidant is added during the vacuum distillation. A preparation method of the antioxidant includes the following steps: extracting a pulverized *Macadamia integrifolia* green peel using ethanol by heat reflux to obtain a green peel extract; extracting the green peel extract using petroleum ether, and then using ethyl acetate; collecting an ethyl acetate layer to obtain the antioxidant. The method can avoid easy oxidation and deterioration of oil during extracting and enriching the palmitoleic acid, and can enrich the palmitoleic acid in the fruit oil of the *Macadamia integrifolia* by not less than 3 times.

7 Claims, No Drawings

METHOD FOR EXTRACTING PALMITOLEIC ACID FROM MACADAMIA INTEGRIFOLIA AND USE THEREOF

This patent application claims the benefit and priority of Chinese Patent Application No. 202110710928.9, filed on Jun. 25, 2021, the disclosure of which is incorporated by reference herein in its entirety.

TECHNICAL FIELD

The present disclosure relates to the technical field of nut-derived fruit oil preparation, in particular to a method for extracting palmitoleic acid from *Macadamia integrifolia* and use thereof.

BACKGROUND

*Macadamia integrifolia* is an edible nut that is high in oil content, nutritious, and crunchy. The edible part of *Macadamia integrifolia* is nut, which can be eaten raw, and has a delicate and crispy mouthfeel, creamy fragrance and excellent flavor after being roasted. The *Macadamia integrifolia* has a fat content reaching not less than 78%, followed by 63% in walnuts, 51% in almonds, 47% in cashew kernels, and only 44.8% in fried peanut kernels. The *Macadamia integrifolia* includes various fatty acids, where unsaturated fatty acids account for 84% of the total fatty acids. The unsaturated fatty acids can maintain the relative fluidity of cell membranes to ensure a normal physiological function of cells, esterify cholesterol and lower blood cholesterol and triglycerides, and involve in synthesis of prostaglandins and thromboxane in the human body as a precursor substance. The unsaturated fatty acids can further reduce blood viscosity and improve blood microcirculation, improve an activity of brain cells, and enhance memory and thinking ability.

Palmitoleic acid, as an ω-7 monounsaturated fatty acid consisting of 16 carbon atoms and having a double bond, plays an important role in nutrition, medicine and industry. There are limited sources of the palmitoleic acid in nature, mainly animal sources (such as whale and cod liver oils), while plants have a limited content of the palmitoleic acid. However, the *Macadamia integrifolia* contains a relatively large amount of the palmitoleic acid. However, there is no research and report on extraction and enrichment of *Macadamia integrifolia*-derived palmitoleic acid in the prior art. At present, the preparation of *Macadamia integrifolia*-derived fruit oil is complicated and lengthy. Moreover, the palmitoleic acid is easily oxidized and deteriorated during a long preparation process, affecting biological effects and product quality. Therefore, there is an urgent need to develop a method for extracting and enriching the palmitoleic acid from kernels of the *Macadamia integrifolia* that can improve a product quality of the palmitoleic acid.

SUMMARY

The present disclosure intends to provide a method for extracting palmitoleic acid from *Macadamia integrifolia*, to avoid easy oxidization and deterioration of oil during extracting and enriching the palmitoleic acid.

To achieve the above objective, the present disclosure adopts the following technical solutions.

The present disclosure provides a method for extracting palmitoleic acid from *Macadamia integrifolia*, including the following steps:

S1: subjecting a fruit oil obtained by cold pressing and extraction from nuts of the *Macadamia integrifolia* to saponification and acidification in sequence to obtain a mixed oil D; and S2: adding an antioxidant to the mixed oil D, conducting vacuum distillation on the mixed oil D, collecting a fraction, washing the fraction, and removing water in the fraction to obtain a mixed oil G; where a preparation method of the antioxidant includes the following steps:

S1': extracting a pulverized *Macadamia integrifolia* green peel using ethanol as an extraction solvent by heat reflux to obtain an ethanol extract; conducting concentration on the ethanol extract to obtain an extract, and dissolving the extract in water to obtain an aqueous solution A;

S2': extracting the aqueous solution A using petroleum ether, and collecting an aqueous layer I to obtain an aqueous solution B; and S3': extracting the aqueous solution B using ethyl acetate, collecting an ethyl acetate layer, and conducting concentration to obtain the antioxidant.

The principle and advantages are: the fat in the fruit oil is decomposed into fatty acid salts through saponification, and the fatty acid salts are converted into fatty acids through acidification. The fractions containing a large amount of palmitoleic acid are collected by vacuum distillation, thereby extracting and enriching the palmitoleic acid. During the vacuum distillation, fatty acids are easily oxidized, and related efficacy may be reduced due to a longer preparation process. Therefore, preferably antioxidants are added to prevent palmitoleic acid from being oxidized during the vacuum distillation. Antioxidants in the prior art can play an antioxidative effect to a certain extent. The *Macadamia integrifolia* green peel extract is used to prevent palmitoleic acid from being oxidized. After a lot of research on the green peel, it is found that an alcoholic extract of the green peel is extracted with the petroleum ether, and an aqueous phase is retained; the retained aqueous phase is further extracted with the ethyl acetate, and an ethyl acetate phase is collected, and the ethyl acetate phase has a better anti-oxidative effect of the palmitoleic acid. However, other extraction parts (such as a petroleum ether extraction part and an n-butanol extraction part) do not have the above effect. It is found that the ethyl acetate extraction part of the green peel has a desirable effect on the antioxidant of fatty acids, and the palmitoleic acid is prepared and extracted based on this, which improves the quality of the palmitoleic acid. The *Macadamia integrifolia* green peel is a discarded part of *Macadamia integrifolia* during processing, and the green peel can be further utilized through the present disclosure. This is novel use of the green peel other than that as a fertilizer, which provides a feasible way for comprehensive utilization of the *Macadamia integrifolia* green peel resources.

Further, in S1', the pulverized *Macadamia integrifolia* green peel may be extracted using the ethanol with a volume fraction of 95% as the extraction solvent by heat reflux for 3 h to obtain the ethanol extract; and the ethanol and the *Macadamia integrifolia* green peel may have a solid-liquid ratio of 500 mL:500 gather components with an antioxidant effect in the green peel can be fully extracted using the above extraction solvent, solid-liquid ratio and extraction method.

Further, in S2', the aqueous solution A may be extracted three times with the petroleum ether; and the petroleum ether and the aqueous solution A may have a volume ratio of 1:1 in each extraction. The aqueous solution A is extracted three times using the petroleum ether, such that relatively strong non-polar parts in the aqueous solution A can be separated into the petroleum ether phase, and parts with the antioxidant effect can still remain in the aqueous phase.

Further, in S3', the aqueous solution B may be extracted three times with the ethyl acetate; and the ethyl acetate and the aqueous solution B may have a volume ratio of 1:1 in each extraction. Ethyl acetate extraction can obtain relatively strong non-polar parts in the aqueous solution B, while relatively strong polar parts have still remained in the aqueous phase. Experimental studies have shown that components extracted from the ethyl acetate phase have a desirable resistance to fatty acid oxidation.

Further, in S1, the fruit oil may be mixed fully with a sodium hydroxide solution, and subjected to a reaction at 50° C. for 4 h, followed by layering to obtain an aqueous layer II and a mixed oil A; a pH value of the aqueous layer II may be adjusted to 5 using a hydrochloric acid solution, and the mixed oil A may be subjected to washing and drying to obtain the mixed oil D. By the above operations, after 4 h of saponification at 50° C., the fat in the fruit oil is fully hydrolyzed to form fatty acid salts and glycerol; the fatty acid salts form fatty acids through acidification; after washing with water, the alkali in the mixed oil of fatty acids is fully cleaned to prepare for the subsequent vacuum distillation.

Further, in S2, the antioxidant in the mixed oil D may have a mass fraction of 1% to 4%. The above dosage of the antioxidant can ensure that the palmitoleic acid is not oxidized and decomposed in large quantities during the preparation.

Further, in S2, the vacuum distillation may be conducted at 80° C. and −60 MPa for 4 h. The above parameters can ensure that the palmitoleic acid is fully distilled, and a product enriched with the palmitoleic acid can be collected in an obtained fraction. Through the above vacuum distillation, a content of the palmitoleic acid in the product can be increased by not less than 3 times.

The present disclosure further provides use of the method for extracting palmitoleic acid from *Macadamia integrifolia*, where the mixed oil G is used for preparing a drug, cosmetics or a health care product.

Palmitoleic acid, as a monounsaturated fatty acid consisting of 16 carbon atoms and having a double bond, is one of the common omega-7 fatty acids in nature. The palmitoleic acid has attracted widespread attention due to a therapeutic effect in some chronic diseases such as metabolic syndrome, diabetes mellitus and inflammation. The palmitoleic acid penetrates the skin quickly, making the skin smooth and non-greasy; at present, the palmitoleic acid has begun to be used in facial skin care, lipstick and baby products, as well as sunscreen products. Studies have also shown that the palmitoleic acid has a strong inhibitory effect on melanin production in mouse melanoma cells; the palmitoleic acid inhibits tyrosinase activity in mouse melanocytes at a protein level, thereby reducing melanin synthesis. Therefore, the palmitoleic acid can be used in preparation of whitening skin care products as an effective whitening agent. The method of the present disclosure can reduce the oxidative deterioration of the palmitoleic acid during the preparation, and greatly improve a quality of the palmitoleic acid products.

Further, the mixed oil G may have a peroxide value of less than 7 meq/kg. Due to the antioxidant derived from the *Macadamia integrifolia* green peel extract, the amount of oxidative decomposition of the fatty acids during the extraction and preparation is reduced, to guarantee the quality of palmitoleic acid to the greatest extent.

Further, the palmitoleic acid in the mixed oil G may have a mass fraction of greater than 50%. The method can enrich the palmitoleic acid, such that a mass fraction thereof can be increased to not less than 50%, thereby meeting the needs of subsequent preparation of medicines, cosmetics and health care products.

DETAILED DESCRIPTION OF THE EMBODIMENTS

The present disclosure is described in more detail below with reference to the specific implementations.

Example 1: Nuts of *Macadamia integrifolia* were pressed for oil by a conventional cold pressing process to obtain a fruit oil. After testing, the fruit oil contained 52.12% of oleic acid and 17.33% of palmitoleic acid. Extraction and enrichment were conducted on palmitoleic acid in the fruit oil. In a reaction kettle, the fruit oil and a sodium hydroxide solution with a solute mass fraction of 1% were added, where the fruit oil and the sodium hydroxide solution had a mass ratio of 1:4. Specifically, 1 kg of the fruit oil was added for extraction and reaction. After fully mixing the fruit oil and the sodium hydroxide solution, reaction was conducted at 50° C. for 4 h, and materials in the reaction kettle had water-oil stratification (where a lower layer was an aqueous layer and an upper layer was a mixed oil A), such that saponification was completed. A 5 mol/L hydrochloric acid solution was added to the materials, a pH value of the aqueous layer was adjusted to 5, and the mixed oil A was collected. In the mixed oil A, pure water was added according to a volume ratio of 3:1, followed by fully mixing and allowing standing for stratification; an oil phase of the upper layer was collected to obtain a mixed oil B. The above water washing was repeated to obtain a mixed oil C. Anhydrous sodium sulfate was added to the mixed oil C, where the anhydrous sodium sulfate in the mixed oil C had a mass fraction of 4%, followed by stirring for 30 min to remove water in the mixed oil C; after filtration, a mixed oil D (mainly containing various fatty acids) was obtained, with a mass of 0.75 kg. An antioxidant was added to mixed oil D, with a mass fraction in the mixed oil D of 3%. The mixed oil D containing the antioxidant was subjected to vacuum distillation at 80° C. and −60 MPa for 4 h in vacuum distillation equipment, and a fraction was collected. In the fraction, pure water was added according to a volume ratio of 5:1, followed by fully mixing and allowing standing for stratification; an oil phase of the upper layer was collected to obtain a mixed oil E. The above water washing was repeated to obtain a mixed oil F. Anhydrous sodium sulfate was added to the mixed oil F, where the anhydrous sodium sulfate in the mixed oil F had a mass fraction of 4%, followed by stirring for 30 min to remove water in the mixed oil F; after filtration, a mixed oil G (mainly containing various fatty acids, mainly palmitoleic acid) was obtained, with a mass of 0.31 kg. After testing, the palmitoleic acid in the mixed oil G had a mass fraction of 53.61%, which increased a content of palmitoleic acid by 3 times.

A preparation method of the antioxidant included the following steps:

500 g of a dried *Macadamia integrifolia* green peel sample (with a moisture content of 15%) was pulverize and added to 500 mL of ethanol with a volume fraction of 95%, extraction was conducted by heat reflux for 3 h, followed by conducting filtration and suction to collect a filtrate. The 95% ethanol was added to conduct reflux, where the materials were refluxed three times in total, and filtrates obtained from the three reflux treatments were combined to obtain an ethanol extract. An obtained green peel ethanol solution was dried to paste to obtain an extract (with a density of 1.31 g/ml), the extract was dissolved in pure water at a solid-to-liquid ratio of 10 g:500 ml, to obtain an aqueous solution A for subsequent use.

The aqueous solution A was extracted by an equal volume of petroleum ether, shaken well, and allowed to stand for extraction for 5 h, and a petroleum ether layer was remained. The extraction was repeated three times, and obtained petroleum ether layers were combined to obtain a petroleum ether extract; an aqueous layer extracted with petroleum ether was remained to obtain an aqueous solution B. The petroleum ether extract was evaporated to dryness to obtain an extract (with a density of 1.20 g/ml), namely a first extract.

The aqueous solution B was extracted by an equal volume of ethyl acetate, shaken well, and allowed to stand for extraction for 5 h, and an ethyl acetate layer was remained; the extraction was repeated three times, and obtained ethyl acetate layers were combined to obtain an ethyl acetate extract; an aqueous layer extracted with ethyl acetate was remained to obtain an aqueous solution C. The ethyl acetate extract was evaporated to dryness to obtain an extract (with a density of 1.35 g/ml), namely a second extract.

The aqueous solution C was extracted by an equal volume of n-butanol, shaken well, and allowed to stand for extraction for 5 h, and an n-butanol layer was remained; the extraction was repeated three times, and obtained n-butanol layers were combined to obtain an n-butanol extract; an aqueous layer extracted with n-butanol was remained to obtain an aqueous solution D. The n-butanol extract was evaporated to dryness to obtain an extract (with a density of 1.33 g/ml), namely a third extract. The aqueous solution D was evaporated to dryness to obtain an extract (with a density of 1.25 g/ml), namely a fourth extract.

The antioxidant used was the second extract. The antioxidant in the mixed oil D had a mass fraction of 3%. According to "GB/T 5009.37-2003, Method for Analysis of Hygienic Standard of Edible Oils, 11 Aug. 2003", a peroxide value of the mixed oil G was tested, and a test result was 5.369 meq/kg. Peroxide value is an indicator of a degree of oxidation for oil and fatty acids, which is used to indicate whether an oil sample has been oxidized and deteriorated, and the peroxides, aldehydes, and ketones and the like produced by oxidation of oil. The peroxide value measures a degree of rancidity of the oil. Generally speaking, a higher peroxide value means higher rancidity. Some small molecular substances produced by the oxidative rancidity of fats and fatty acids have adverse effects on the human body, such as generation of free radicals. Therefore, oil with excessively high peroxide value may have a negative impact on the body health.

Example 2: it was basically the same as Example 1, but a mass fraction of an antioxidant in a mixed oil D was adjusted to 1%. A peroxide value of a mixed oil G is detected to be 6.320 meq/kg, and palmitoleic acid in the mixed oil G has a mass fraction of 51.21%.

Example 3: it was basically the same as Example 1, but a mass fraction of an antioxidant in a mixed oil D was adjusted to 4%. A peroxide value of a mixed oil G is detected to be 5.014 meq/kg, and palmitoleic acid in the mixed oil G has a mass fraction of 52.36%.

Comparative Example 1: basically the same as Example 1, but an antioxidant was replaced with the first extract. A peroxide value of a mixed oil G was detected to be 10.544 meq/kg.

Comparative Example 2: basically the same as Example 1, but an antioxidant was replaced with the third extract. A peroxide value of a mixed oil G was detected to be 12.752 meq/kg.

Comparative Example 3: basically the same as Example 1, but an antioxidant was replaced with the fourth extract. A peroxide value of a mixed oil G was detected to be 11.710 meq/kg.

Comparative Example 4: basically the same as Example 1, but no antioxidant was used. A peroxide value of a mixed oil G was detected to be 18.322 meq/kg.

Comparative Example 5: basically the same as Example 1, but an antioxidant was replaced with a rosemary extract (80% rosmarinic acid). A peroxide value of a mixed oil G was detected to be 5.018 meq/kg.

In summary, in Examples 1-3, a novel antioxidant (the second extract of *Macadamia integrifolia* green peel) was used during extraction of palmitoleic acid from the fruit oil. Therefore, during the vacuum distillation, the fatty acid components in the fruit oil can be well protected from oxidative rancidity, to guarantee a quality of the palmitoleic acid obtained by extraction. The second extract is derived from the ethyl acetate extraction part of the green peel extract; however, the antioxidant effect of the petroleum ether extraction part and the n-butanol extraction part of the green peel extract in the vacuum distillation of palmitoleic acid is not as desirable as that of the ethyl acetate extraction part. The method can enrich the palmitoleic acid in the fruit oil of *Macadamia integrifolia* by not less than 3 times, with a simple process and no complex and expensive instruments required. The produced palmitoleic acid has a better quality; a prepared mixed oil containing the palmitoleic acid can be used in preparation and use of food, health care products or cosmetics, to exert whitening, antihypertensive and hypoglycemic effects of the palmitoleic acid.

The commonly used rosemary extract in the prior art can also achieve a better antioxidant effect. However, the rosemary extract needs to be purchased additionally, increasing a production cost. While the *Macadamia integrifolia* green peel is a discarded part of *Macadamia integrifolia* during processing, and the green peel can be further utilized through the present disclosure. This is novel use of the green peel other than that as a fertilizer, which provides a feasible way for comprehensive utilization of the *Macadamia integrifolia* green peel resources.

The above are only examples of the present disclosure, and common knowledge such as specific structures and characteristics known in the art is not described here too much. It should be noted that those skilled in the art may further make several variations and improvements without departing from the scope of the present disclosure, but such variations and improvements should also be deemed as falling within the protection scope of the present disclosure without affecting the implementation effect and practicability of the patent. The protection scope claimed in this application shall be based on contents of claims, and disclosure in the specification such as the detailed description may be used to interpret the contents of the claims.

What is claimed is:

1. A method for extracting palmitoleic acid from *Macadamia integrifolia*, comprising the following steps:
    S1: subjecting a fruit oil obtained by cold pressing and extraction from nuts of the *Macadamia integrifolia* to saponification and acidification in sequence to obtain a mixed oil D; and
    S2: adding an antioxidant to the mixed oil D, conducting vacuum distillation on the mixed oil D, collecting a fraction, washing the fraction, and removing water in the fraction to obtain a mixed oil G; wherein a preparation method of the antioxidant comprises the following steps:

S1': extracting a pulverized *Macadamia integrifolia* green peel using ethanol as an extraction solvent by heat reflux to obtain an ethanol extract; conducting concentration on the ethanol extract to obtain an extract, and dissolving the extract in water to obtain an aqueous solution A;

S2': extracting the aqueous solution A using petroleum ether, and collecting an aqueous layer I to obtain an aqueous solution B; and S3': extracting the aqueous solution B using ethyl acetate, collecting an ethyl acetate layer, and conducting concentration to obtain the antioxidant.

2. The method for extracting palmitoleic acid from *Macadamia integrifolia* according to claim 1, wherein in S1', the pulverized *Macadamia integrifolia* green peel is extracted using the ethanol with a volume fraction of 95% as the extraction solvent by heat reflux for 3 h to obtain the ethanol extract; and the ethanol and the *Macadamia integrifolia* green peel have a solid-liquid ratio of 500 mL:500 g.

3. The method for extracting palmitoleic acid from *Macadamia integrifolia* according to claim 2, wherein in S2', the aqueous solution A is extracted three times with the petroleum ether; and the petroleum ether and the aqueous solution A have a volume ratio of 1:1 in each extraction.

4. The method for extracting palmitoleic acid from *Macadamia integrifolia* according to claim 3, wherein in S3', the aqueous solution B is extracted three times with the ethyl acetate; and the ethyl acetate and the aqueous solution B have a volume ratio of 1:1 in each extraction.

5. The method for extracting palmitoleic acid from *Macadamia integrifolia* according to claim 4, wherein in S1, the fruit oil is mixed fully with a sodium hydroxide solution, and subjected to a reaction at 50° C. for 4 h, followed by layering to obtain an aqueous layer II and a mixed oil A; a pH value of the aqueous layer II is adjusted to 5 using a hydrochloric acid solution, and the mixed oil A is subjected to washing and drying to obtain the mixed oil D.

6. The method for extracting palmitoleic acid from *Macadamia integrifolia* according to claim 5, wherein in S2, the antioxidant in the mixed oil D has a mass fraction of 1% to 4%.

7. The method for extracting palmitoleic acid from *Macadamia integrifolia* according to claim 6, wherein in S2, the vacuum distillation is conducted at 80° C. and −60 MPa for 4 h.

\* \* \* \* \*